United States Patent
Solis

(10) Patent No.: US 9,788,895 B2
(45) Date of Patent: *Oct. 17, 2017

(54) BASKET CATHETER WITH DEFLECTABLE SPINE

(71) Applicant: BIOSENSE WEBSTER (ISRAEL) LTD., Yokneam (IL)

(72) Inventor: Mario A. Solis, Rancho Cucamonga, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/344,445

(22) Filed: Nov. 4, 2016

(65) Prior Publication Data

US 2017/0071665 A1  Mar. 16, 2017

Related U.S. Application Data

(63) Continuation of application No. 14/960,254, filed on Dec. 4, 2015, now Pat. No. 9,486,282, which is a
(Continued)

(51) Int. Cl.
  *A61B 5/042* (2006.01)
  *A61B 18/14* (2006.01)
  (Continued)

(52) U.S. Cl.
  CPC ........ *A61B 18/1492* (2013.01); *A61B 5/0422* (2013.01); *A61B 5/6858* (2013.01);
  (Continued)

(58) Field of Classification Search
  CPC ................ A61B 5/0422; A61B 5/1492; A61B 2018/00267
  See application file for complete search history.

(56) References Cited

U.S. PATENT DOCUMENTS

| 5,313,943 A | 5/1994 | Houser et al. |
| 5,391,199 A | 2/1995 | Ben-Haim |

(Continued)

FOREIGN PATENT DOCUMENTS

| WO | 9502995 A1 | 2/1995 |
| WO | 9605768 A1 | 2/1996 |

(Continued)

OTHER PUBLICATIONS

Extended European Search Report dated Jan. 22, 2015 issued in Application No. EP 14184785.5, 7 pages.

*Primary Examiner* — Lee S Cohen
(74) *Attorney, Agent, or Firm* — Lewis Roca Rothgerber Christie LLP

(57) ABSTRACT

A catheter adapted for mapping and/or ablation in the atria has a basket-shaped electrode array with two or more location sensors with a deflectable expander. The catheter has comprises a catheter body, a basket electrode assembly at a distal end of the catheter body, and a control handle at a proximal end of the catheter body. The basket electrode assembly has a plurality of electrode-carrying spines and an expander that is adapted for longitudinal movement relative to the catheter body for expanding and collapsing the assembly via a proximal end portion extending past the control handle that can be pushed or pulled by a user. The expander is also adapted for deflection in responsive to an actuator on the control handle that allows a user to control at least one puller wire extending through the catheter body and the expander.

20 Claims, 9 Drawing Sheets

Related U.S. Application Data continuation of application No. 14/028,435, filed on Sep. 16, 2013, now Pat. No. 9,204,929.

(51) Int. Cl.
*A61M 25/01* (2006.01)
*A61M 25/00* (2006.01)
*A61B 5/00* (2006.01)
A61B 17/00 (2006.01)
A61B 18/00 (2006.01)

(52) U.S. Cl.
CPC .... *A61M 25/0082* (2013.01); *A61M 25/0147* (2013.01); *A61B 2017/00323* (2013.01); *A61B 2018/00267* (2013.01); *A61B 2018/00351* (2013.01); *A61B 2018/00577* (2013.01); *A61B 2018/00642* (2013.01); *A61B 2018/00839* (2013.01); *A61B 2018/1467* (2013.01); *A61B 2562/0209* (2013.01); *A61B 2562/04* (2013.01); *A61M 2025/015* (2013.01)

(56) References Cited

U.S. PATENT DOCUMENTS

| | | |
|---|---|---|
| 5,443,489 A | 8/1995 | Ben-Haim |
| 5,480,422 A | 1/1996 | Ben-Haim |
| 5,546,951 A | 8/1996 | Ben-Haim |
| 5,558,091 A | 9/1996 | Acker et al. |
| 5,568,809 A | 10/1996 | Ben-haim |
| 5,702,438 A | 12/1997 | Avitall |
| 5,772,590 A | 6/1998 | Webster, Jr. |
| 5,846,238 A | 12/1998 | Jackson et al. |
| 5,848,972 A | 12/1998 | Triedman et al. |
| 6,024,739 A | 2/2000 | Ponzi et al. |
| 6,064,905 A | 5/2000 | Webster, Jr. et al. |
| 6,071,282 A | 6/2000 | Fleischman |
| 6,216,043 B1 | 4/2001 | Swanson et al. |
| 6,430,426 B2 | 8/2002 | Avitall |
| 6,640,119 B1 | 10/2003 | Budd et al. |
| 6,748,255 B2 | 6/2004 | Fuimaono et al. |
| 6,771,996 B2 | 8/2004 | Bowe et al. |
| 6,917,834 B2 | 7/2005 | Koblish et al. |
| 6,973,340 B2 | 12/2005 | Fuimaono et al. |
| 7,269,453 B2 | 9/2007 | Mogul |
| 7,377,906 B2 | 5/2008 | Selkee |
| 7,429,261 B2 | 9/2008 | Kunis et al. |
| 7,522,950 B2 | 4/2009 | Fuimaono et al. |
| 8,137,308 B2 | 3/2012 | Schultz |
| 8,588,885 B2 | 11/2013 | Hall et al. |
| 8,825,130 B2 | 9/2014 | Just et al. |
| 9,204,929 B2 | 12/2015 | Solis |
| 9,486,282 B2 * | 11/2016 | Solis .................... A61B 5/0422 |
| 2010/0114087 A1 | 5/2010 | Edwards et al. |

FOREIGN PATENT DOCUMENTS

| | | |
|---|---|---|
| WO | 9724983 A2 | 7/1997 |
| WO | 9829033 A1 | 7/1998 |

* cited by examiner

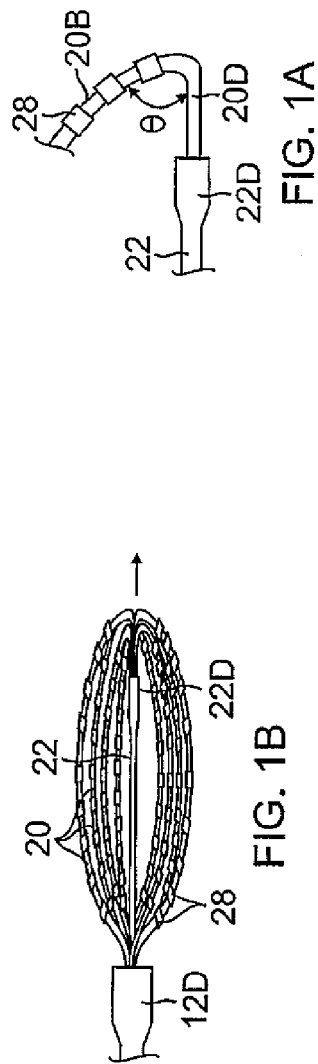
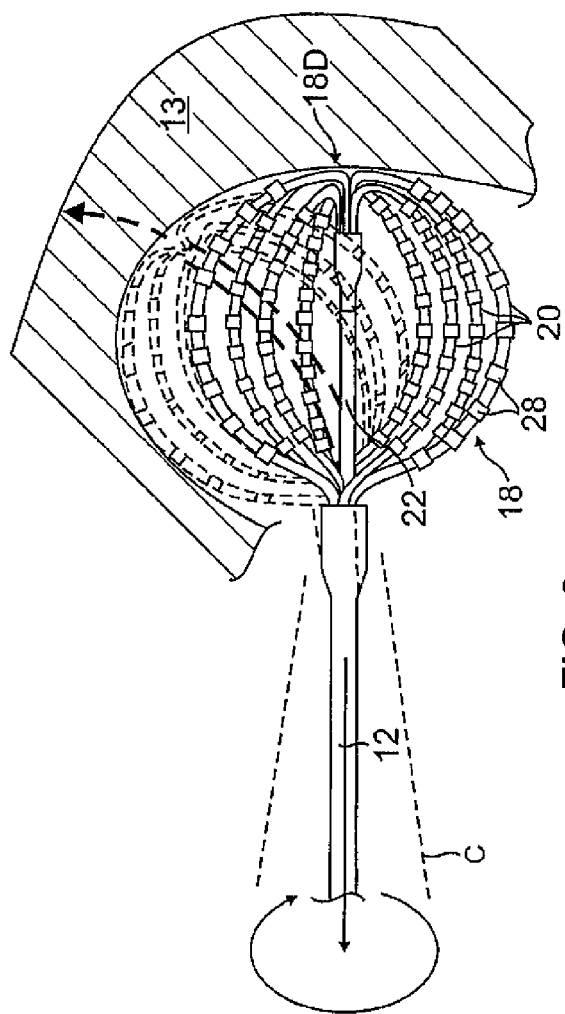
FIG. 1A
FIG. 1B
FIG. 2

BASKET CATHETER WITH DEFLECTABLE SPINE

CROSS-REFERENCE TO RELATED APPLICATIONS

This application is a continuation of and claims priority to and the benefit of U.S. patent application Ser. No. 14/960,254 filed Dec. 4, 2015, issued as U.S. Pat. No. 9,486,282, which is a continuation of U.S. patent application Ser. No. 14/028,435, filed Sep. 16, 2013, issued as U.S. Pat. No. 9,204,929, the entire contents of which are incorporated herein by reference.

FIELD OF INVENTION

This invention relates to electrophysiologic (EP) catheters, in particular, EP catheters for mapping and/or ablation in the heart.

BACKGROUND

Electrophysiology catheters are commonly-used for mapping electrical activity in the heart. Various electrode designs are known for different purposes. In particular, catheters having basket-shaped electrode arrays are known and described, for example, in U.S. Pat. Nos. 5,772,590, 6,748,255 and 6,973,340, the entire disclosures of both of which are incorporated herein by reference.

Basket catheters typically have an elongated catheter body and a basket-shaped electrode assembly mounted at the distal end of the catheter body. The basket assembly has proximal and distal ends and comprises a plurality of spines connected at their proximal and distal ends. Each spine comprises at least one electrode. The basket assembly has an expanded arrangement wherein the spines bow radially outwardly and a collapsed arrangement wherein the spines are arranged generally along the axis of the catheter body. The catheter may further comprise a distal location sensor mounted at or near the distal end of the basket-shaped electrode assembly and a proximal location sensor mounted at or near the proximal end of the basket-shaped electrode assembly. In use, the coordinates of the distal location sensor relative to those of the proximal sensor can be determined and taken together with known information pertaining to the curvature of the spines of the basket-shaped mapping assembly to find the positions of the at least one electrode of each spine.

It is desirable that a basket assembly be capable of detecting in a single beat most or all of the electrical function of the left or right atrium. However, because the atria of an individual patient may vary in size and shape, it is desirable that the basket assembly be sufficiently versatile and steerable to conform to the particular atrium. Conventional basket catheters have an intermediate deflectable section that is proximal of the basket assembly, but the basket assembly itself is typically without steerability or deflectability. As such, the basket assembly often lacks sufficient maneuverability and stability to provide useful contract with enough atrial tissue at any in any single instance. Accordingly it is desirable that a catheter have a basket assembly with improved maneuverability for better tissue contact, especially in a cavernous region of the heart, including an atrium.

SUMMARY OF THE INVENTION

The catheter of the present invention provides the EP physician with a unique tool capable of detecting in a single beat all electrical functions of the left or right atrium. The catheter advantageously has a multi-electrode assembly with a steerable elongated expander, wherein the expander is sufficiently sturdy to support the assembly so as to maintain all the electrodes adjustably disseminated around the expander for enabling contact with surrounding atrial tissue. Puller wires for steering the expander are anchored distal of the electrode assembly so as to provide improved control and placement of the assembly via the control handle. The improved expander also supports the assembly such that the electrodes in the distal portion of the assembly can remain in contact with atrial tissue regardless of the contractions and relaxation cycles of the atria, thus providing physicians with more constant monitoring and accurate readings on electrical readings and recordings of the heart. With the multitude of electrodes carried on the assembly, the catheter provides the physician instant and simultaneous view of all electrical functions within an atrial cavity at a much higher percentage of contact with atrial tissue.

The present invention is directed to a catheter having a basket-shaped electrode array with two or more location sensors with a deflectable expander to provide improved mapping and ablation capabilities. In one embodiment, the catheter comprises a catheter body, a basket electrode assembly at a distal end of the catheter body, and a control handle at a proximal end of the catheter body. The basket electrode assembly has a plurality of electrode-carrying spines and an expander that is adapted for longitudinal movement relative to the catheter body for expanding and collapsing the assembly via a proximal end portion extending past the control handle that can be pushed or pulled by a user. The expander is also adapted for deflection in responsive to an actuator on the control handle that allows a user to control at least one puller wire extending through the catheter body and the expander. The catheter may provide a single puller wire for uni-directional deflection of the expander or two puller wires for bi-directional deflection. Whereas the degree of curvature of the spines changes similarly (or "symmetrically") between all the spines when the expander is moved longitudinally relative to the catheter body, the degree of curvature of the spines changes differently (or "asymmetrically") between the spines when the expander is deflected. When the expander is moved longitudinally, the assembly as a whole expands or collapses so that the curvature of each spine is affected similarly by the movement. However, when the expander is deflected, each spine and its curvature are affected differently by the deflection, with the curvature in selected spines generally increasing and the curvature in opposite spines generally decreasing. The catheter is therefore particularly adapted for mapping and/or ablating in a cavernous region of the heart, including the atria.

In one embodiment, the catheter has a proximal junction at the distal end of the catheter body between the catheter body and the expander, wherein the proximal junction includes a tubing whose proximal end is mounted over the distal end of the catheter body, a ring inside the distal end of the tubing, and a tunnel member is positioned in the through-hole, wherein the tunnel member has a lumen through which the expander extends and is afforded longitudinal movement.

In one embodiment, the catheter has a distal junction at the distal end of the expander, wherein the distal junction includes an outer tubing, a ring inside the outer tubing and a puller wire anchor member.

In one embodiment, the spines are mounted in about 360 radial degrees around the expander. In another embodiment, the spines are mounted in about 180 radial degrees around the expander.

In one embodiment, at least one spine carries at least one ring electrode. In another embodiment, the expander carries at least one ring electrode distal of the distal end of the catheter body.

In one embodiment, the expander has a guidewire lumen.

BRIEF DESCRIPTION OF THE DRAWINGS

These and other features and advantages of the present invention will be better understood by reference to the following detailed description when considered in conjunction with the accompanying drawings wherein:

FIG. 1A is a detailed view of a distal portion of a spine of an electrode assembly of FIG. 1.

FIG. 1B is a detailed view of the electrode assembly of FIG. 1 in a collapsed position.

FIG. 2 is a side view of a catheter of the present invention in contact with atrial issue.

DETAILED DESCRIPTION OF THE INVENTION

Figure 1:
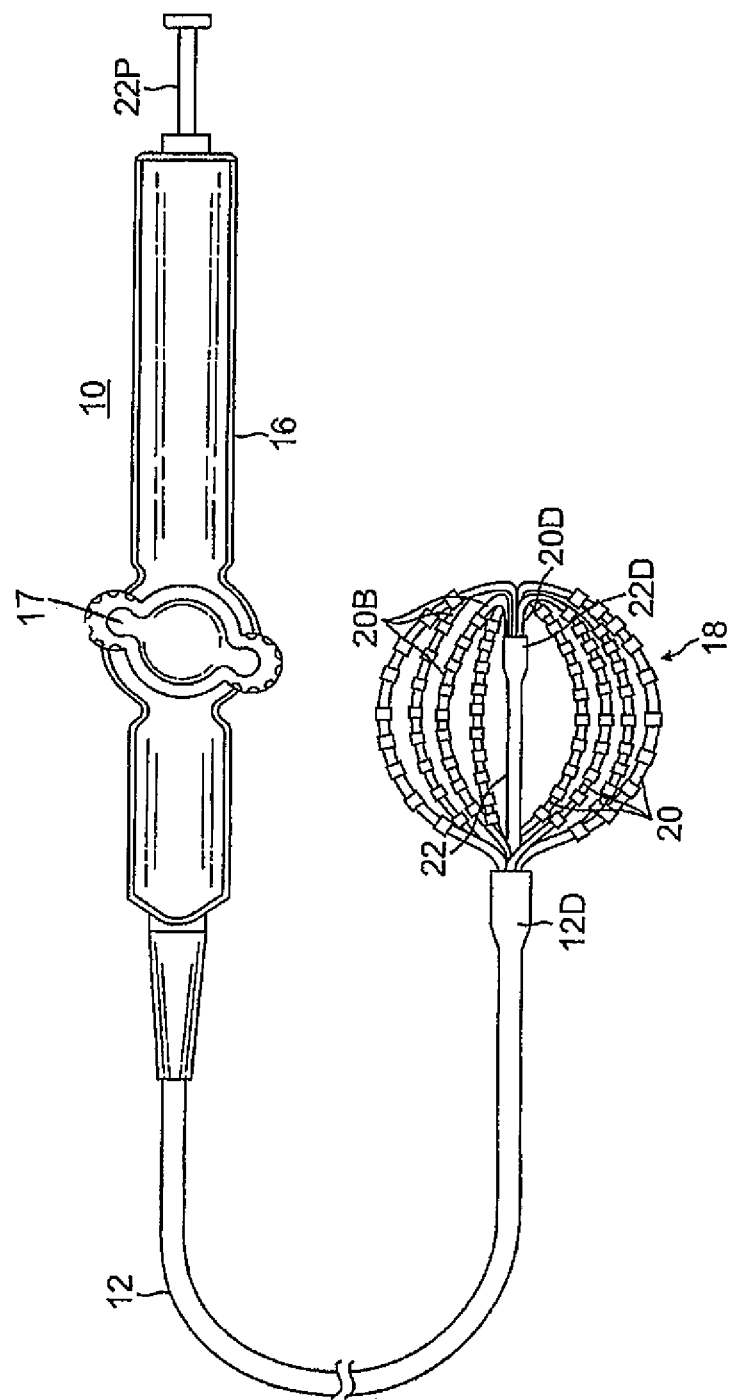
FIG. 1 is a top plan view of a catheter of the present invention, according to one embodiment.

The invention is directed to a catheter 10 having a basket-shaped electrode assembly 18 with an expander 22 providing deflection capabilities. As shown in FIG. 1, the catheter 10 comprises an elongated catheter body 12 having proximal and distal ends and a control handle 16 at the proximal end of the catheter body, with the deflectable basket-shaped electrode assembly 18 being mounted at the distal end of the catheter body 12.

The catheter body 12 comprises an elongated tubular construction having a single, axial or central lumen (not shown), but can optionally have multiple lumens if desired. The catheter body 12 is flexible, i.e., bendable, but substantially non-compressible along its length. The catheter body 12 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 12 so that, when the control handle 16 is rotated, the distal end of the catheter body will rotate in a corresponding manner.

The outer diameter of the catheter body 12 is not critical, but may be no more than about 8 french, more preferably 7 french. Likewise the thickness of the outer wall is not critical, but is preferably thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

The basket-shaped electrode assembly 18 is mounted to the distal end of the catheter body 12. As shown in FIG. 2, the basket-shaped electrode assembly 18 comprises at plurality of spines 20 or arms (e.g., between about five to ten, and preferably about eight) mounted, generally evenly-spaced in about 360 radial degrees around the expander 22 so that the expander forms the center longitudinal axis of the electrode assembly. The spines 20 are all attached, directly or indirectly, to the expander 22 at their distal ends, and to the catheter body 12 at their proximal ends. In accordance with a feature of the present invention, a distal end 22D of the expander 22 is located inside or inwardly of the spines 20 where the distal end 22D of the expander is generally encircled or surrounded by the spines 20.

Figure 3:
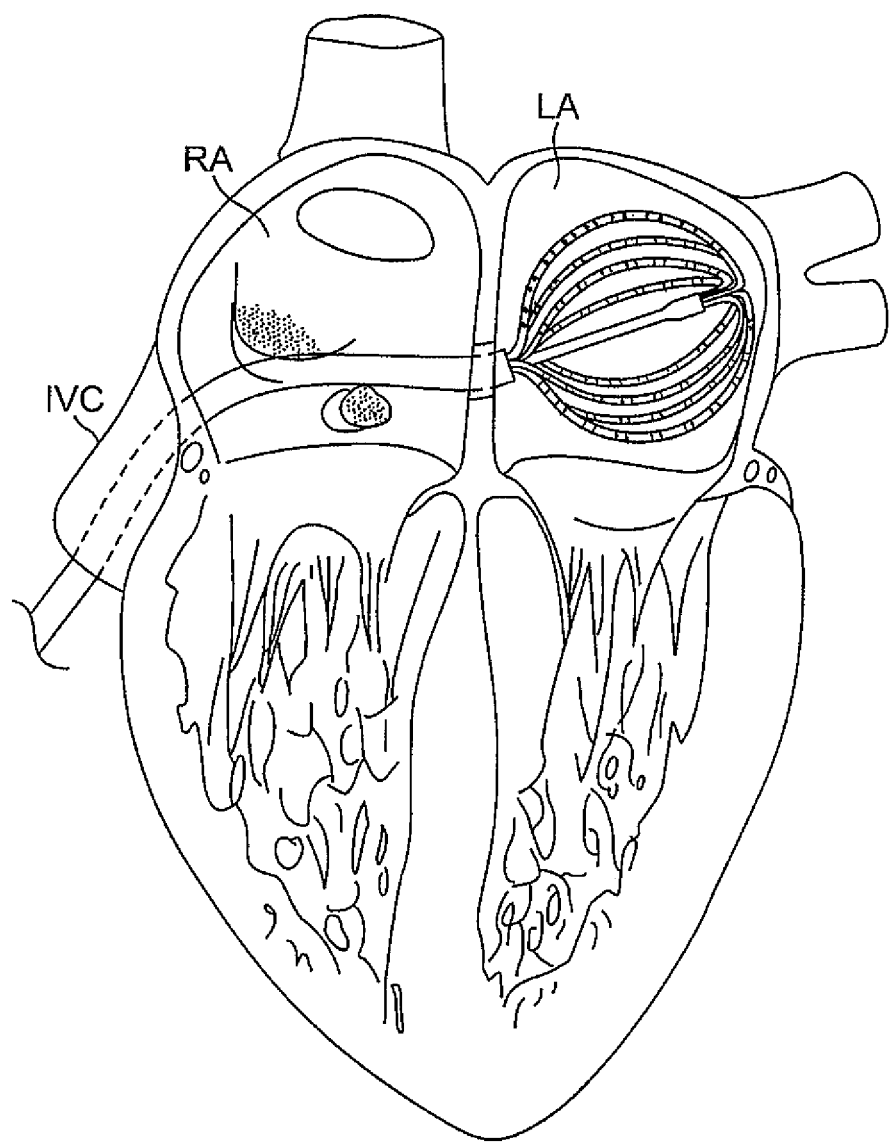
FIG. 3 is a schematic view of the electrode assembly of FIG. 1 deployed in the left atrium.

With reference to FIG. 1A, each spine has a bowed, electrode-bearing portion 20B and a generally straight distal portion 20D. The distal portion 20D is generally coaxial with the expander 22. The bowed portion 20B is adapted to extend at an angle θ from the distal portion 20D, where the angle θ ranges between about 30 degrees (such as when the electrode assembly 18 is elongated and collapsed with the expander 22 extended distally, see FIG. 1B) and 80 degrees (such as when the electrode assembly 18 is deployed and radially expanded with the expander drawn proximally, see FIG. 1). As shown in FIGS. 2 and 3, with the distal end 22D of the expander being in the interior of the assembly 18, the assembly 18 provides a generally smooth profile at its distal end without any protrusion that may otherwise project and puncture tissue 13 in the atrium. Moreover, with a generally smooth profile at its distal end, the assembly 18 can be pivoted in a circular motion where its longitudinal axis traces a cone C to improve electrode contact with minimum risk of damage to tissue, especially in a cavernous region, such as an atrium.

As described in more detail below, the expander 22 is moved longitudinally relative to the catheter body 12 to radially expand or contract the electrode assembly 18, so that in the radially expanded position the spines 20 bow outwardly (FIG. 1) and in the elongated position the spines less bowed and straighter (FIG. 1B). As will be recognized by one skilled in the art, the number of spines 20 can vary as desired depending on the particular application, so that the assembly 18 has at least two spines, preferably at least three spines, and as many as eight or more spines. As used herein, the term "basket-shaped" in describing the electrode assembly 18 is not limited to the depicted configuration, but can include other designs, such as spherical or egg-shaped designs, that include a plurality of expandable arms connected, directly or indirectly, at their proximal and distal ends.

Figure 4:
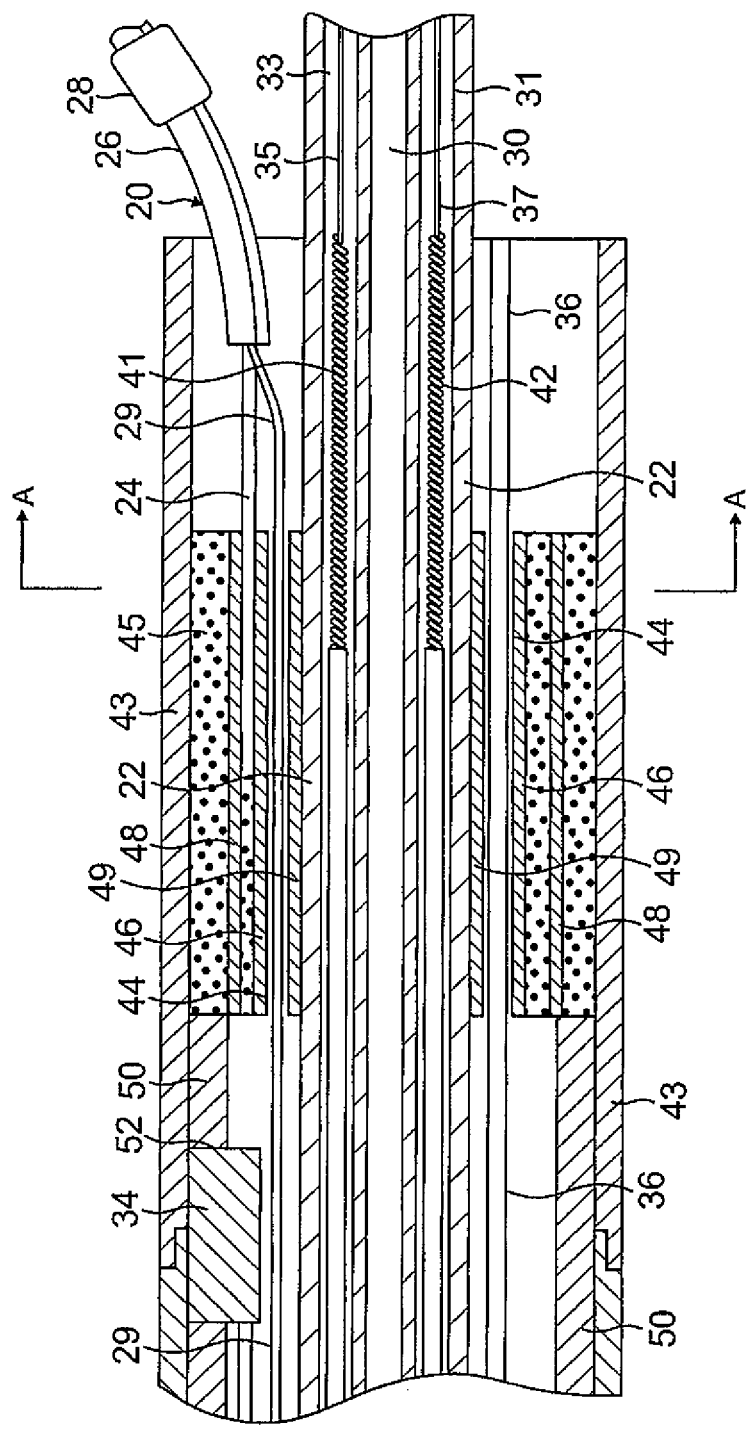
FIG. 4 is a side cross-sectional view of a proximal junction between a distal end of a catheter body and a proximal end of the electrode assembly, affording longitudinal movement of the expander, according to one embodiment of the present invention.

With reference to FIG. 4, each spine 20 comprises a flexible wire 24 with a non-conductive covering 26 on which one or more ring electrodes 28 are mounted. In an embodiment, the flexible wires 24 each comprise a flat Nitinol wire, and the non-conductive coverings 26 each comprise a biocompatible plastic tubing, such as polyurethane or polyimide tubing. Alternatively, the spines 20 can be designed without the internal flexible wire 24 if a sufficiently rigid nonconductive material is used for the non-conductive covering 26 to permit radial expansion of the electrode assembly 18, so long as the spine has an outer surface that is non-conductive over at least a part of its surface for mounting of the ring electrodes 28.

Each of the ring electrodes 28 on the spines 20 is electrically connected to an appropriate mapping or monitoring system and/or source of ablation energy by means of an electrode lead wire 29. Each electrode lead wire 29 extends through the control handle 16, through a lumen in the catheter body 12, and into the non-conductive covering 26 of the corresponding spine 20. Each lead wire 29 is attached to its corresponding ring electrode 28 by any suitable method.

One method for attaching a lead wire 29 to a ring electrode 28 involves first making a small hole through the wall of the non-conductive covering 26. Such a hole can be created, for example, by inserting a needle through the non-conductive covering 26 and heating the needle sufficiently to form a permanent hole. The lead wire 29 is then drawn through the hole by using a microhook or the like. The end of the lead wire 29 is then stripped of any coating and welded to the underside of the ring electrode 28, which is then slid into position over the hole and fixed in place with polyurethane glue or the like. Alternatively, each ring electrode 28 is formed by wrapping a lead wire 29 around the non-conductive covering 26 a number of times and stripping the lead wire of its own insulated coating on its outwardly facing surfaces.

As shown in FIG. 4, the expander 22 is generally coaxial with the catheter body 12. The expander 22 has a distal end that is interior of the assembly 18 and proximal of the distal end of the electrode assembly 18. The expander 22 has a suitable length such that it has a proximal end 22P (FIG. 1) that is exposed proximally of the control handle 16, a longer proximal portion that extends through a central lumen catheter body 12, and a shorter exposed distal portion extending distally of the catheter body 12 and through the assembly 18. The expander 22 is afforded longitudinal movement relative to the catheter body so that it can move the distal ends of the spines 20 proximally or distally relative to the catheter body 12 to radially expand and contract, respectively, the electrode assembly. The expander 22 comprises a material sufficiently rigid to achieve this function. In an embodiment, the expander 22 comprises braided polyimide tubing 23, i.e., tubing having inner and outer layers of polyimide with a braided stainless steel mesh therebetween, as is generally known in the art.

Figure 5:
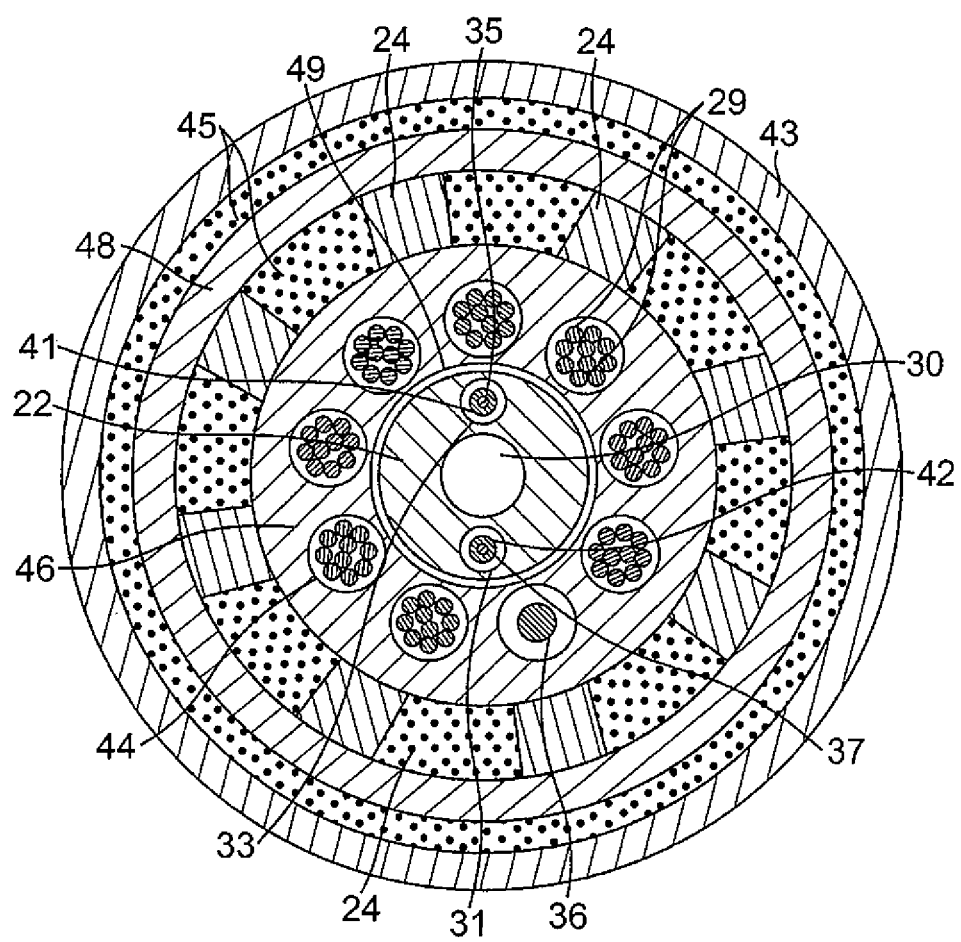
FIG. 5 is an end cross-sectional view of the proximal junction of FIG. 4, taken along line A-A.

With reference to FIGS. 4 and 5, the expander 22 has a center, on-axis guidewire lumen 30 that extends along its entire length. As understood in the art, the guidewire lumen 30 permits a guidewire to extend through the entire length of the catheter for introduction of the catheter 10 into a patient's body. Additionally, in accordance with a feature of the present invention, the expander 22 also has at least one off-axis lumen 31 for uni-directional deflection, or also a second, diametrically-opposite, off-axis lumen 33 for bi-directional deflection, of the assembly 18. Puller wire 35 extends through lumen 33 and puller wire 37 extends through lumen 31. The proximal ends of the puller wires are anchored in the control handle 16 to be controlled by a deflection actuator 17 (FIG. 1). The distal end of each puller wire is anchored at or near the distal end 22D of the expander 22, as described below. Surrounding each puller wire 35 and 37 is a respective compression coil 41 and 42. Each compression coil has a proximal end at or near the junction between the control handle 16 and the catheter body 12, and a distal end at or near the distal end of the catheter body 12. Accordingly, when a selected puller wire on one side of the expander is drawn proximally by manipulation of the deflection actuator 17, the compression coil of that puller wire extending through the catheter body 12 resists compression along its length so that the puller wire deflects the expander 22 distal of the catheter body 12 to that side of the expander. In accordance with a feature of the present invention, deflecting the expander 22 can change the degree of bowing in the spines 20. In the illustrated embodiment of FIG. 2, the degree of bowing increases (with the spines having greater curvature) on the side of the deflection and the degree of bowing decreases (with the spines having lesser curvature) on the side opposite the deflection. For example, the increase in bowing advantageously enables the spines to exert greater pressure on the atrial tissue for better contact between the tissue and the electrodes on the spines. Thus, a user can change the shape of the electrode assembly by adjusting the longitudinal extension or withdrawal of the expander and/or by adjusting the direction and degree of deflection of the expander. In that regard, longitudinal extension or withdrawal of the expander results in radially symmetrical change or adjustment in the electrode assembly with the degree of curvature of each spine being affected similarly, whereas deflection of expander results in radially asymmetrical changes with the degree of curvature of each spine being affected differently depending on their position relative to the deflection of the expander.

An embodiment of a proximal junction between the proximal end of the electrode assembly 18 and distal end of the catheter body 12 is shown in FIGS. 4 and 5. In FIG. 4, only one spine 20 of the electrode assembly 18 is shown for clarity. The junction includes a short plastic housing or tubing 43, which may be made of PEEK (polyetheretherketone). The housing 43 joins the distal end of the catheter body 12 and proximal end of the electrode assembly 18. In one embodiment, the plastic housing 43 has a length of about 11 mm. If the plastic housing 43 is too long, it can disadvantageously affect the flexibility of the distal end of the catheter body. The proximal end of the plastic housing 43 is mounted on the distal end of the catheter body 12 by any suitable method, for example, with polyurethane glue or the like.

The proximal junction also includes an outer proximal ring 48 inside the housing 43, and a tunnel member 46 in a center through-hole xx of the ring 48. Proximal ends of the flexible Nitinol wires 24 are mounted, for example, evenly-spaced, between the outer proximal ring 48 and the tunnel member 46, both of which may be made of polyimide. The outer proximal ring 48 and the tunnel member 46 may be relatively short, e.g., about 3 mm in length, compared to the length of the housing 43. The tunnel member 46 provides the electrode lead wires 29 with longitudinal movement within the catheter body 12 so that they do not break when the catheter body 12 bends. To that end, the tunnel member 46 has multiple off-axis lumens 44 through which the lead electrodes 29 extend and are allowed longitudinal movement. The lumens 44 may be equally spaced radially around the tunnel member 46. The tunnel member 46 also has a center lumen 49, through which the expander 22 extends and is allowed longitudinal movement. The outer proximal ring 48, the proximal ends of the wires 24 and the tunnel member 46 may be held in place in the proximal junction with polyurethane glue 45 or the like. The proximal ends of the non-conductive coverings 26 of the spines 20 also extend into the plastic housing 43, but proximal ends of the wires 24 are stripped of the coverings 26 so that only the exposed wires 24 are mounted and anchored between the tunnel member 46 and outer proximal ring 48.

Figure 6:
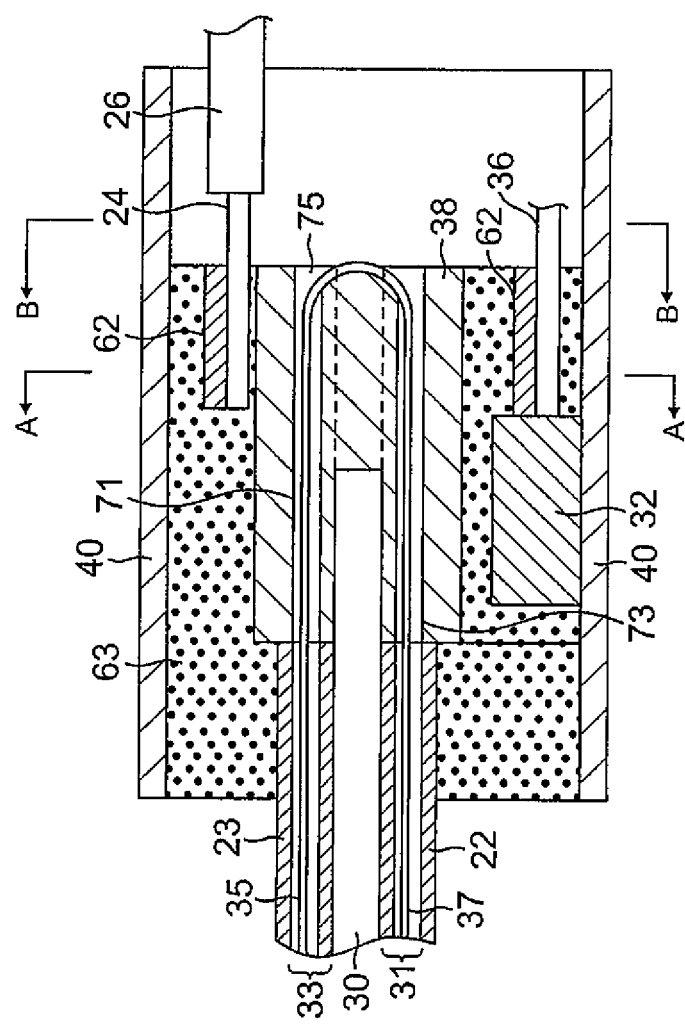
FIG. 6 is a side cross-sectional view of a distal junction between distal ends of the expander and the spines of the electrode assembly, in accordance with one embodiment of the present invention.
Figure 7:
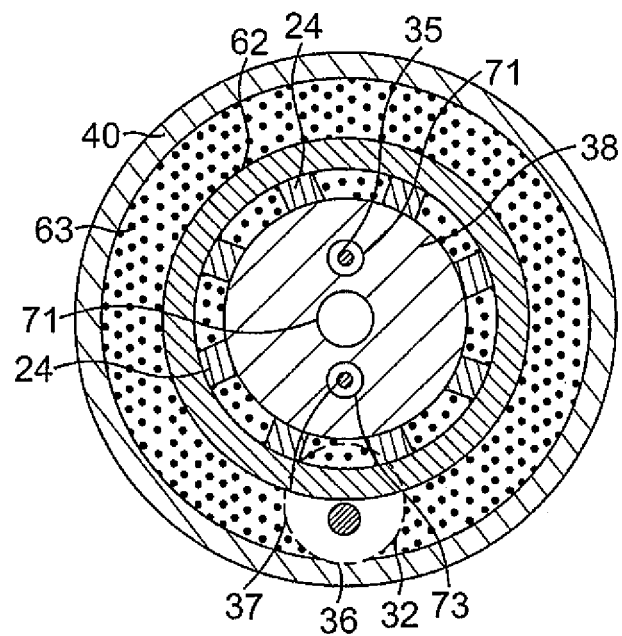
FIG. 7 is an end cross-sectional view of the distal junction of FIG. 6, taken along line A-A.
Figure 8:
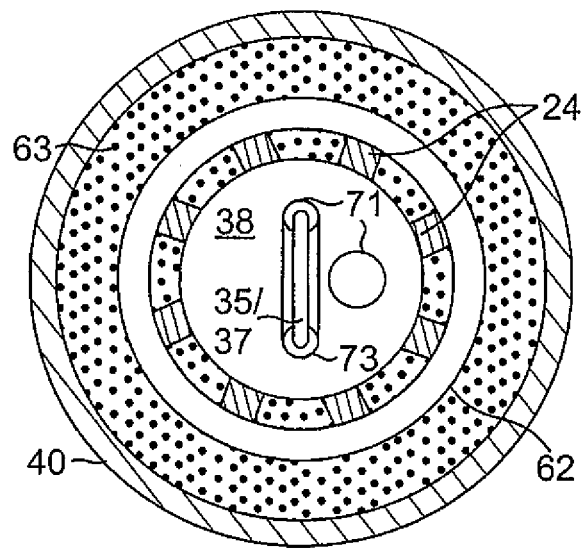
FIG. 8 is an end view of the distal junction of FIG. 6, taken along line B-B.
Figure 9:
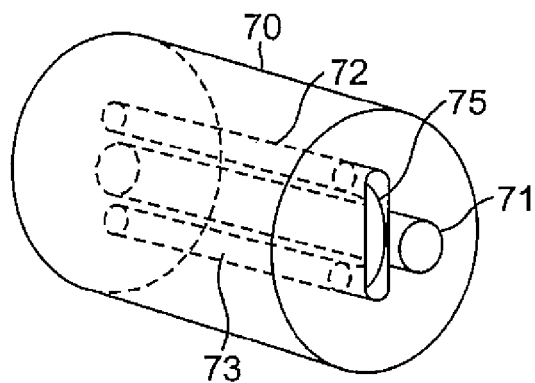
FIG. 9 is a perspective view of a puller wire anchor member, in accordance with one embodiment.

An embodiment of a distal junction between the distal end of the expander 22 and the distal ends of the spines 20 is depicted in FIGS. 6, 7 and 8. In FIG. 6, only one spine 20 of the assembly 18 is shown for clarity. The distal junction includes an outer tubing 40, which may be made of polyurethane or polyimide. The distal end 22D of the expander extends into the outer tubing 40 where it abuts with a proximal face of a puller wire anchor member 38. In the disclosed embodiment, the member 38 has a generally solid cylindrical body 70 with a guidewire lumen 71 that is generally axially aligned with the guidewire lumen 30 of the expander 22. The member 38 also has two diametrically opposed, off-axis lumens 71 and 73 that are generally axially aligned with the lumens 31 and 33, respectively, of the expander. A U-shaped channel 75 is formed in a distal end of the body 70 which extends between the lumens 71 and 73. Accordingly, the puller wires 35 and 37 may be a continuous single tensile member that wraps around the distal end of the member 38 via the channel 75. This continuous pathway for the puller wire occupies minimal space in the distal junction and obviates the need to separately anchor each distal end of two puller wires. It is noted that the guidewire lumen 71 in the member 38 may have a slight bend off the longitudinal axis to accommodate the U-shaped channel 75, or vice versa where the U-shaped channel 75 may be situated slightly off-center to accommodate the guidewire lumen 71.

With reference to FIGS. 6, 7 and 8, a ring 62 shorter than the outer tubing 40 sits in the tubing 40 and surrounds at least a distal portion of the member 38. The ring 62 may be made of metal or plastic. The distal ends of the flexible Nitinol wires 24 that form the spines 20 are mounted, for example, evenly-spaced, between the generally rigid ring 42 and the member 38. The outer tubing 40 covers the entire distal junction. The distal junction, including the outer tubing 40, the ring 42, the member 38, as well as the distal ends of the wires 24, is held together by polyurethane glue 63 or the like. The outer tubing 40 longer than the member 38, so that its proximal end extends over the distal end of the expander 22 and its distal end extends beyond the distal end of the member 38. The proximal end of the outer tubing 40 reinforces the attachment between the expander and the member 38. The non-conductive coverings 26 of the wires 24 extend into the outer tubing 40 but distal ends of the flexible wires 24 are stripped of the coverings 26 so that only the exposed wires 24 are mounted and anchored between the ring 42 and the member 38.

With the proximal and distal junctions anchoring the proximal and distal ends of the spines 20, the expander 22 can extend or withdraw each spine relative to the distal end of the catheter body 12. The proximal junction affords longitudinal movement of the expander 22 while anchoring the proximal ends of the spines 20. The distal junction anchors the distal ends of the spines 20 to the distal end 22D of the expander so that they are responsive to movement of the expander. Advantageously, the distal junction is proximal of the distal end of the electrode assembly 18 and interior of the electrode assembly 18 such that the electrode assembly has a generally smooth distal surface and profile so that the distal end of the electrode assembly can contact tissue. Moreover, the rounded distal end of the electrode assembly allows the assembly to be pivoted or moved in a circular motion (with the longitudinal axis of the assembly tracing a cone C, as shown in FIG. 2) to contact circumferentially-surrounding tissue.

Figure 10:
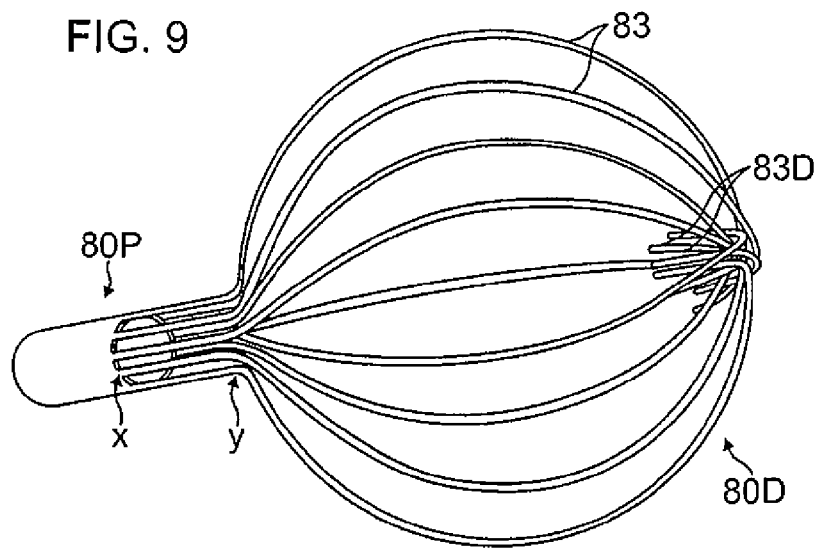
FIG. 10 is a perspective view of an electrode assembly support structure, in accordance with one embodiment.
Figure 10A:
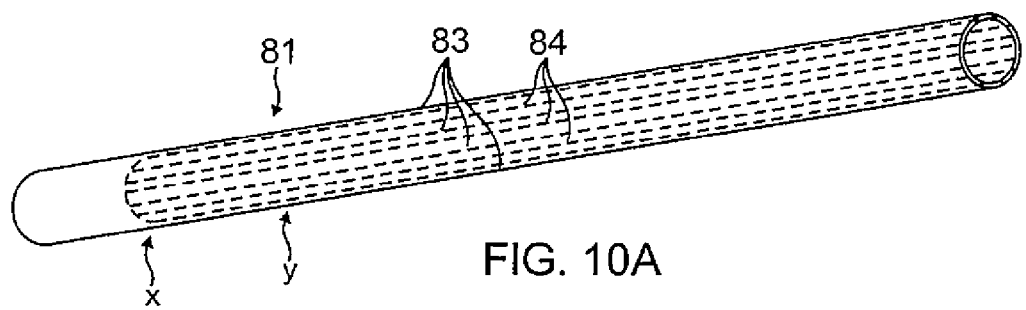
FIG. 10A is a perspective view of a hollow cylindrical body from which the electrode assembly support structure of FIG. 10 is formed.

FIGS. 10 and 10A show an electrode assembly support structure 80 that is formed from a hollow cylindrical body 81 that is precision-cut, e.g., laser cut, and shaped to a structure having a proximal stem portion 80P and a distal basket portion 80D. A plurality of parallel elongated spine supports 83 extending along the length of the body 81 are formed by cutting and removing parallel elongated strips 84 that extend from a first location X in the stem portion 80P to the distal end of the cylindrical body 81. A significant distal portion of each spine support is bowed, or otherwise bent outwardly with a curvature, at a second location Y distal of the first location X to form the basket-shape of the assembly 18. A straight distal end portion 83D of each spine support is bent inwardly toward the proximal stem portion 80P for attachment to the distal end of the expander by a distal junction. The proximal stem may be inserted into the distal end of the catheter body up to the second location Y and attached thereto by a proximal junction to allow for longitudinal movement of the expander 22. To that end, the stem portion 80P may be mounted between the proximal outer ring 48 and the tunnel member 46. The structure 80 is constructed of any suitably rigid material with shape material, e.g., Nitinol, so as to allow the structure to be flexible, elastic and sufficiently rigid to hold a predetermined configuration, yet be deformable under an applied force and able to resume the predetermined configuration upon removal of the applied force.

The catheter further includes two location sensors 32 and 34 for providing location information about each of the ring electrodes 28 on the electrode assembly 18. A proximal location sensor 34 is mounted within the proximal junction, in the housing 43. And the distal location sensor 32 is mounted in the distal junction, in the outer tubing 40.

Each location sensor 32 and 34 is connected to a corresponding sensor cable 36 that extends through the catheter body 12 and control handle 16 and out the proximal end of the control handle within an umbilical cord (not shown) to a sensor control module (not shown) that houses a circuit board (not shown). Alternatively, the circuit board can be housed within the control handle 16, for example, as described in U.S. Pat. No. 6,024,739, the disclosure of which is incorporated herein by reference. The sensor cable 36 comprises multiple wires encased within a plastic covered sheath. In the sensor control module, the wires of the sensor cable are connected to the circuit board. The circuit board amplifies the signal received from the corresponding location sensor and transmits it to a computer in a form understandable by the computer by means of the sensor connector at the proximal end of the sensor control module. Also, because the catheter is designed for single use only, the circuit board may contain an EPROM chip that shuts down the circuit board approximately twenty-four hours after the catheter has been used. This prevents the catheter, or at least the location sensor, from being used twice.

In one embodiment, each location sensor 32 and 34 comprises a magnetic-field-responsive coil, as described in U.S. Pat. No. 5,391,199, or a plurality of such coils, as described in International Publication WO 96/05768. The plurality of coils enables six-dimensional position and orientation coordinates to be determined. Alternatively, any suitable position sensor known in the art may be used, such as electrical, magnetic or acoustic sensors. Suitable location sensors for use with the present invention are also described, for example, in U.S. Pat. Nos. 5,558,091, 5,443,489, 5,480,422, 5,546,951, and 5,568,809, and International Publication Nos. WO 95/02995, WO 97/24983, and WO 98/29033, the disclosures of which are incorporated herein by reference. In one embodiment, an electromagnetic mapping sensor has a length of from about 3 mm to about 7 mm, preferably about 4 mm.

Alternatively, one of the location sensors 32 and 34 can comprise a bend sensor, which generates signals responsive to a bend radius of the spines 20. Such a bend sensor can comprise one or more piezoelectric sensors, as are known in the art, which generate electrical signals proportional to a force or torque exerted thereon when the catheter bends. Alternatively, a bend sensor can comprise one or more strain sensors, as are known in the art, or a fiber optic sensor, wherein the bend radius is determined by measuring the loss and/or back-reflection of light in an optical fiber, as is also known in the art.

The coordinates of the distal sensor 32, relative to those of the proximal sensor 34, are determined and taken together with other known information pertaining to the curvature of the spines 20 of the basket-shaped mapping assembly 18. This information is used to find the positions of the ring electrodes 28 mounted on the spines 20.

In the depicted embodiment of FIG. 4, the proximal location sensor is situated in a second tunnel 50 provided at the proximal junction. Proximal end of the second tunnel extends into the catheter body 12 and distal end of the second tunnel extends into the housing 43. The tunnel 50 may be made of polyimide and has a length ranging from about 5 to 7 mm. The tunnel 50 protects the expander 22, electrode lead wires 29 and the sensor cable 36 that is attached to the distal location sensor 32 from being glued to the catheter at the junction of the catheter body 12 and housing 43 during assembly. Prior to assembly, the proximal location sensor 34 is mounted in a window 52 of the second tunnel 50. The proximal location sensor may have a length of about 1 to 3 mm. The sensor cable 36 attached to the proximal location sensor 34 extends through the second tunnel 50 and catheter body 12 along with the other components. Accordingly, the cable 36 for the proximal sensor is afforded longitudinal movement at the proximal junction.

The distal location sensor 32 is mounted at or near the distal end of the electrode assembly 18. In the depicted embodiment of FIG. 6, the distal location sensor is mounted between the outer tubing 44 and the member 38 and held in place by the glue 63. The sensor cable 36 attached to the distal location sensor 32 extends through one of the nonconductive coverings 26 and into the distal end of the catheter body 12.

As would be recognized by one skilled in the art, other arrangements for constructing the proximal and distal junctions and for mounting the location sensors could also be used in accordance with the invention.

Deflection of the expander 22 relative to the catheter body 12, which results in deflection of the electrode assembly 18, is accomplished by manipulation of the control handle 16. As shown in FIG. 1, the control handle 16 comprises a generally cylindrical housing in which mechanisms are provided for actuating uni- or bi-directional deflection of the expander. In the illustrated embodiment, the control handle has a deflection arm 18 adapted for the user to manipulate the puller wires 35 and 37 for deflecting the expander bi-directional. Rotation of the deflection arm 18 to one direction deflects the expander in that direction. Rotation of the deflection arm 18 to the opposite direction deflects expander in the opposite direction. A suitable control handle is described in U.S. Pat. No. 7,377,906, entitled STEERING MECHANISM FOR BI-DIRECTIONAL CATHETER and U.S. Pat. No. 8,137,308, entitled CATHETER WITH ADJUSTABLE DEFLECTION SENSITIVITY, the entire disclosures of which are hereby incorporated by reference.

Figure 11:
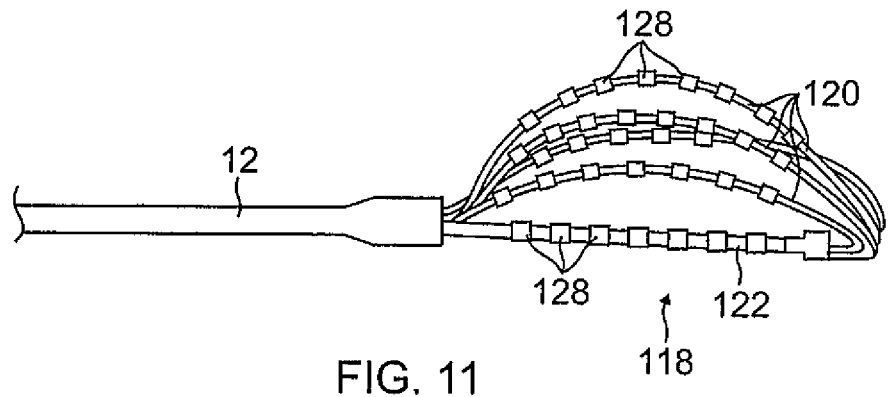
FIG. 11 is a side view of an electrode assembly of the present invention, in accordance with another embodiment.
Figure 11A:
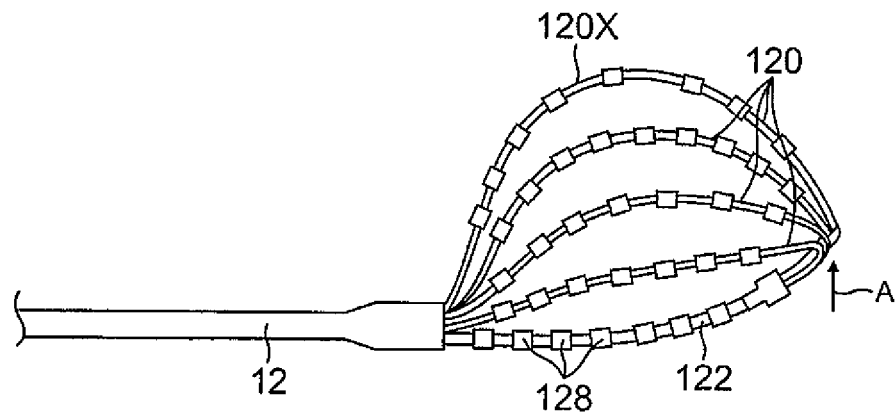
FIG. 11A is a side view of the electrode assembly of FIG. 11, with the expanded deflected.

In an alternate embodiment as shown in FIG. 11, electrode assembly 118 comprises a plurality of spines 120 or arms (e.g., between about three to five, and preferably about four) mounted, for example, generally evenly-spaced, in about 180 radial degrees around expander 122. The spines 120 are all attached, directly or indirectly, to the expander 122 at their distal ends, and to the catheter body 112 at their proximal and distal ends, as described above. In the illustrated embodiment of FIG. 11A, the degree of bowing increases (with the spines having greater curvature) on the side of the deflection and the degree of bowing decreases (with the spines having lesser curvature) on the side opposite the deflection. Thus, a user can change the shape of the electrode assembly by adjusting the longitudinal extension or withdrawal of the expander and/or by adjusting the direction and degree of deflection of the expander 122.

Figure 11B:
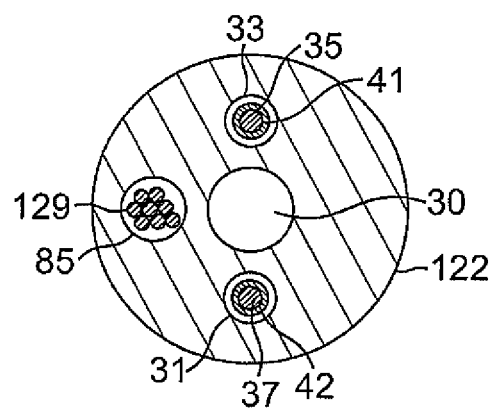
FIG. 11B is an end cross-sectional view of the expander of FIG. 11, in accordance with one embodiment.

The expander 122 of assembly 118 may also carry a plurality of ring electrodes 128 in addition to those carried on the spines. As shown in FIG. 11B, tubing 123 of the expander 122 includes a fourth lumen 85 through which lead wires 129 extend. As such, the expander spine 122 is adapted for tissue contact in addition to providing support and deflection to the basket assembly 118.

To use the catheter of the invention, an electrophysiologist introduces a guiding sheath, guidewire and dilator into the patient, as is generally known in the art. A suitable guiding sheath for use in connection with the inventive catheter is the PREFACE™ Braided Guiding Sheath (commercially available from Biosense Webster, Inc., Diamond Bar, Calif.). The guidewire is inserted, the dilator is removed, and the catheter is introduced through the guiding sheath whereby the guidewire lumen in the expander permits the catheter to pass over the guidewire. As shown in FIG. 3, the catheter is first introduced to the right atrium RA via the inferior vena cava IVC, where it passes through the septum S in order to reach the left atrium LA.

The guiding sheath covers the spines of the electrode assembly in a collapsed position so that the entire catheter can be passed through the patient's vasculature to the desired location. The expander may be positioned distally of the catheter body to allow the spines of the assembly to be flattened while the assembly is passed through the guiding sheath. Once the distal end of the catheter reaches the desired location, e.g., the left atrium, the guiding sheath is withdrawn to expose the electrode assembly. The expander is drawn proximally or otherwise manipulated so that the spine flex outwardly between the distal and proximal junctions. With the electrode assembly radially expanded, the ring electrodes contact atrial tissue. As recognized by one skilled in the art, the electrode assembly can be fully or partially expanded, straight or deflected, in a variety of configurations depending on the configuration of the region of the heart being mapped.

Using the ring electrodes on the spines (and/or the expander) in combination with the distal end proximal location sensors 32 and 34, the electrophysiologist can map local activation time and/or ablate, which can guide the electrophysiologist in diagnosing and providing therapy to the patient. The catheter can include one or more reference ring electrodes mounted on the catheter body, or one or more reference electrodes can be placed outside the body of the patient. By using the inventive catheter with the multiple electrodes on the basket-shaped electrode assembly, the electrophysiologist can obtain a true anatomy of a cavernous region of the heart, including an atrium, by measuring less points than with traditional catheters, allowing him to map the region more quickly. Moreover, the electrophysiologist can pivot the electrode assembly about its distal end such that the longitudinal axis of the assembly sweeps out a cone to readily bring more radial ring electrodes into contact with surrounding tissue for mapping and/or ablation without fear of puncturing tissue. Furthermore, by deflecting the expander, selected ring electrodes can be easily brought into contact with atrial tissue for improved sensing and ablation.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
   an elongated catheter body having proximal and distal ends and at least one lumen therethrough;
   an electrode assembly at the distal end of the catheter body, the electrode assembly having proximal and distal ends and comprising a plurality of spines, the spines comprising a plurality of electrodes;
   an expander having proximal and distal ends, the expander forming a longitudinal axis of the assembly, the spines attached at their proximal ends to the catheter body and at their distal ends to the expander;
   at least one puller wire that extends through the expander, the puller wire having a distal end anchored in the expander at a location distal of the distal end of the catheter body and proximal of the distal end of the assembly;
   at least one proximal location sensor and at least one distal location sensor; and
   a control handle proximal of the catheter body, the control handle having an actuator adapted to move the at least one puller wire,
   wherein the electrode assembly has an expanded arrangement when the expander is moved proximally along the longitudinal axis relative to the catheter body and the electrode assembly has a collapsed arrangement when the expander is moved distally along the longitudinal axis relative to the catheter body, and
   wherein the expander is adapted to deflect in at least one direction when the at least one puller wire is moved by the actuator.

2. The catheter of claim 1, further comprising a proximal junction at the distal end of the catheter body, the proximal junction comprising:
   a tubing having a proximal end and a distal end, the proximal end being mounted over the distal end of the catheter body;
   a ring inside the distal end of the tubing, the ring having a through-hole; and
   a tunnel member in the through-hole of the ring,
   wherein the tunnel member has a lumen through which the expander extends and has longitudinal movement.

3. The catheter of claim 2, wherein the tunnel member has at least one off-axis lumen.

4. The catheter of claim 2, further comprising a distal junction at the distal end of the expander, the distal junction comprising:
   an outer tubing having a lumen;
   a puller wire anchor in the lumen of the outer tubing; and
   a ring in the lumen of the outer tubing,
   wherein distal ends of spine support members are anchored between the ring and the puller wire anchor.

5. The catheter of claim 4, wherein the at least one proximal location sensor is in the proximal junction and the at least one distal location sensor is in the distal junction.

6. The catheter of claim 1, wherein the spines are mounted in about 360 radial degrees around the expander.

7. The catheter of claim 1, wherein the spines are mounted in about 180 radial degrees around the expander.

8. The catheter of claim 1, wherein at least one spine carries at least one ring electrode.

9. The catheter of claim 1, wherein the expander carries at east one ring electrode distal of the distal end of the catheter body.

10. The catheter of claim 1, wherein the expander has a guidewire lumen.

11. A catheter comprising:
    an elongated catheter body having proximal and distal ends and at least one lumen therethrough, the catheter body defining a longitudinal axis;
    an electrode assembly at the distal end of the catheter body, the electrode assembly having proximal and distal ends and comprising a plurality of spines, the spines comprising a plurality of electrodes;
    an expander having proximal and distal ends, the expander forming a longitudinal axis of the assembly, the spines attached at their proximal ends to the catheter body and at their distal ends to the expander;
    at least one puller wire that extends through the expander, the puller wire having a distal end anchored in the expander at a location distal of the distal end of the catheter body and proximal of the distal end of the assembly; and
    a control handle proximal of the catheter body, the control handle having an actuator adapted to move the at least one puller wire,
    the expander having a proximal end portion extending past a proximal end of the control handle,
    wherein the expander is adapted for longitudinal movement relative to the catheter body and for deflection relative to the longitudinal axis.

12. The catheter of claim 11, wherein the electrode assembly is adapted to assume an expanded configuration in response to longitudinal movement of the expander relative to the catheter body.

13. The catheter of claim 11, wherein the electrode assembly is adapted to assume an asymmetrical configuration in response to deflection of the expander relative to the longitudinal axis.

14. The catheter of claim 11, wherein each spine is adapted to assume a bowed configuration with a degree of curvature.

15. The catheter of claim 14, wherein the degree of curvature of each spine changes similarly in response to longitudinal movement of the expander relative to the catheter body.

16. The catheter of claim 14, wherein the degree of curvature of each spine changes differently in response to deflection of the expander relative to the catheter body.

17. The catheter of claim 11, further comprising a distal junction between a distal end of the expander and distal ends of the spines, wherein the distal junction is proximal of a distal end of the electrode assembly.

18. The catheter of claim 11, wherein the spines are mounted in about 360 radial degrees around the expander.

19. The catheter of claim 11, wherein the spines are mounted in about 180 radial degrees around the expander.

20. The catheter of claim 11, wherein at least one spine carries at least one ring electrode.

* * * * *